United States Patent
Jay

(10) Patent No.: US 7,415,381 B2
(45) Date of Patent: Aug. 19, 2008

(54) JOINT FRICTION SENSING

(75) Inventor: Gregory D. Jay, Norfolk, MA (US)

(73) Assignee: Rhode Island Hospital, A LifeSpan Partner, Providence, RI (US)

(*) Notice: Subject to any disclaimer, the term of this patent is extended or adjusted under 35 U.S.C. 154(b) by 177 days.

(21) Appl. No.: 10/754,337

(22) Filed: Jan. 9, 2004

(65) Prior Publication Data

US 2004/0143415 A1 Jul. 22, 2004

Related U.S. Application Data

(60) Provisional application No. 60/438,849, filed on Jan. 9, 2003.

(51) Int. Cl.
*G01C 9/00* (2006.01)

(52) U.S. Cl. ..................................... 702/151

(58) Field of Classification Search ............. 702/33–35, 702/40–43, 94, 95, 138, 139, 150–153
See application file for complete search history.

(56) References Cited

U.S. PATENT DOCUMENTS

2004/0146593 A1* 7/2004 Han et al. .................. 424/773

FOREIGN PATENT DOCUMENTS

SU      740242   *  6/1980
SU     1053819   * 11/1983

OTHER PUBLICATIONS

English Translation of SU 740 242, Jun. 15, 1980.*

Mabuchi, K. et al., "Use of Robotics Technology to Measure Friction in Animal Joints", Clinical Biomechanics vol. 11, No. 3, pp. 121-125, 1996.

Charnley, John, "The Lubrication of Animal Joints", 1959, Symposium on Biomechanica, pp. 12-20.

Bahabri, et al., *Arthritis Rheum.*, 41(4):730-735 (1998).

Clark, et al., *J. Anat.*, 195 (Pt. 1):45-56 (1999).

Flannery, et al., *Biochem. Biophys. Res. Comm.*, 234(3):535-541 (1999).

Forster, et al., *Proc. Inst. Mech. Eng.*, 213(H4):329-345 (1999).

Good, et al., *J. Biomed. Mater. Res.*, 33(4):275-283 (1996).

(Continued)

*Primary Examiner*—Michael P Nghiem
(74) *Attorney, Agent, or Firm*—Clark & Elbing LLP

(57) ABSTRACT

A system for determining an indication of animal joint mobility includes a mounting apparatus configured to hold a first condyle of the joint stationary in a position such that a second condyle of the joint can pivot about the joint, a pendulum configured to be coupled to the second condyle and configured such that a portion of a weight of the pendulum is disposed below a pivot axis of the joint such that the pendulum and second condyle can oscillate about the pivot axis, an angular displacement indicator associated with the pendulum, an angular displacement recorder configured to store indicia of the angular displacement, as indicated by the angular displacement indicator; of the pendulum over time, and a processor coupled to the angular displacement recorder and configured to use the angular displacement indicia to determine a first value associated with momentum decay of oscillations of the pendulum and to use the at least one value to determine a second value associated with a coefficient of friction of the joint.

11 Claims, 8 Drawing Sheets

OTHER PUBLICATIONS

Higaki, et al., *Proc. Inst. Mech. Eng.*, 212(H5):337-346 (1998).
Jay, et al., *J. Rheumatol.*, 27(3):594-600 (2000).
Jay, et al., *Glycoconjugate J.*, 18:807-815 (2001).
Marcelino, et al., *Nature Genet.*, 23(3):319-322 (1999).
Murakami, et al., *Proc. Inst. Mech. Eng.*, 212(H1):23-35 (1998).
Swann, et al., *Biochem. J.*, 161:473-485 (1977).
Wang, et al., *Biomaterials*, 17(9):865-871 (1996).
Zhou, et al., *IEEE Trans. Biomed. Eng.*, 44(7):620-633 (1997).

* cited by examiner

JOINT FRICTION SENSING

CROSS-REFERENCE TO RELATED ACTIONS

This application claims the benefit of U.S. Provisional Application No. 60/438,849 filed Jan. 9, 2003, which is incorporated here by reference.

FIELD OF THE INVENTION

The invention relates to determining the coefficient of friction of a joint, in particular an animal joint.

BACKGROUND OF THE INVENTION

Friction reduction of animal joints is mediated by the superficial zone of the articular cartilage and by the lubricating ability of synovial fluid. Up until recently, no human diseases were clearly associated with a lack of chondroprotection by lubrication. Camptodactyly-arthroapthy-coxa vara-pericarditis (CACP) syndrome is an autosomal recessive pre-pubertal form of osteoarthrosis. The arthropathy is non-inflammatory in nature and appears histologically similar to osteoarthritis. This disease has been linked to a locus on chromosome 1q25 which expresses megakaryocyte stimulating factor (MSF; GenBank U70136). Expression of this gene also leads to both superficial zone protein expressed by chondrocytes and lubricin by synovial fibroblasts. Lubricin is a classical mucinous glycoprotein (5) providing boundary lubrication of apposed cartilaginous surfaces in the absence of viscosity. Lubricin is 50% (w/w) glycosylated with multiple residues of O-linked $\beta$(1-3)Gal-GalNAc which provides for lubricating activity (6). A CACP/lubricin knockout mouse was created that lacked the orthologous gene PRG4 for producing lubricin.

Presently, new investigational devices and drugs designed to improve or prevent arthritis are tested in animals with histological measures and in people with visual analog pain scales. There is presently no comprehensive joint function model with which to test molecules with a posited therapeutic benefit.

SUMMARY OF THE INVENTION

Embodiments of the invention provide techniques to simulate animal articular movement. Measurements obtained allow calculation of the coefficient of friction between surfaces of two tissues, e.g., cartilage surfaces.

An exemplary device contains a pendulum driver adapted to receive a mammalian joint. The device also contains a photodetector or a video camera. The photo detector and/or video camera record images of the joint in movement and thereby permit calculation of pendulum velocity.

Preferably, the exemplary device is configured to receive explanted joints from animal models of arthritic disease. The joint represents the pivot point of a pendulum. For example, a device adapted to measure joint mobility of joints excised from a mouse includes a pendulum ranging in length from 10-20 cm, e.g., the pendulum arm is 15 cm in length. For rabbits, the pendulum is 20-40 cm in length. A bob is used to apply a load to the joint to be tested. The weight of the bob is approximately equal (or greater than) to the weight of the animal from which the joint was excised. For some measurements, the joint is overloaded, i.e., the weight of the bob exceed the weight of the animal from which the joint was obtained (e.g., the bob weighs 2%, 5%, 10%, 50%, and up to 100% more than the weight of the animal. For a mouse knee joint, the weight of the bob ranges from 10-30 gm, e.g., the bob weighs 20 gm. For a rabbit joint, e.g., a rabbit stifle, the weight of a bob is approximately 4 pounds or 2 kg.

One condyle is stationary, while the other condyle is weighted, e.g., by affixing a bob. A condyle is a bone, e.g., a tibia bone or femur bone that participates in an articulating joint. For example, the lower condyle of a knee joint is immobilized in the device, and the upper condyle of the joint is weighted from below. The condyles are reversible. For example, in one configuration the tibia is immobilized and the femur is weighted, and in another configuration, the femur is immobilized and the tibia is weighted.

An exemplary method according to the invention for evaluating mobility of an animal joint includes applying a force to an intact mammalian joint ex vivo, videographically recording a swing amplitude and swing cycle number, and determining a pendulum velocity. Pendulum velocity is directly correlated to mobility of the mammalian joint.

Also within the invention is a method of evaluating mobility of a joint in vivo. To take measurements of a joint of a living animal, the animal is sedated. Optionally, the animal is intubated for administration of anesthetics, gases, medicaments, or other compositions. One bone of an articulating joint, e.g., the femur of a knee joint, is immobilized and the animal's body fixed while the tibia is weighted. Force is applied to the joint and measurements taken as described above.

Embodiments of the invention may be used to evaluate the effect of therapeutic intervention on joint mobility as well as to screen compounds to identify those which improve joint mobility, e.g., compounds that reduce the symptoms of arthritic diseases. For example, a method of evaluating mobility of a mammalian joint may be carried out by applying a force to a mammalian joint in the presence and in the absence of a candidate compound; videographically recording a swing amplitude and swing cycle number; and determining a rate of deceleration. A decrease in the rate of deceleration in the presence of the candidate compound compared to that in the absence of the candidate compound indicates that the candidate compound increases mobility of a mammalian joint.

With exemplary embodiments of the invention, the synovium of a joint remains intact, and medicaments to be evaluated may be injected directly into synovial space prior to testing. Alternatively, a medicament is administered to an animal prior to sacrificing the animal and removing the joint for testing. Genetically-altered animals, e.g., ones in which a target gene has mutated, may be tested to evaluate the role of the target gene in mobility. For example, knockout mice, i.e., mice that fail to express a target gene product due to the absence or mutation of the corresponding gene, are evaluated to determine whether the gene has an effect on joint mobility.

In general, in an aspect, the invention provides a system for determining an indication of animal joint mobility, the system including a mounting apparatus configured to hold a first condyle of the joint stationary in a position such that a second condyle of the joint can pivot about the joint, a pendulum configured to be coupled to the second condyle and configured such that a portion of a weight of the pendulum is disposed below a pivot axis of the joint such that the pendulum and second condyle can oscillate about the pivot axis, an angular displacement indicator associated with the pendulum, an angular displacement recorder configured to store indicia of the angular displacement, as indicated by the angular displacement indicator; of the pendulum over time, and a processor coupled to the angular displacement recorder and configured to use the angular displacement indicia to determine a first value associated with momentum decay of oscillations of the pendulum and to use the at least one value to determine a second value associated with a coefficient of friction of the joint.

Implementations of the invention may include one or more of the following features. The first value is an acceleration associated with the pendulum. The second value is the coefficient of friction of the joint. A weight of the pendulum is at least approximately an average weight of a type of the animal associated with the joint. The angular displacement indicator includes an apparatus configured to project an angle-dependent pattern of light toward the pendulum, and a reflector coupled to the pendulum configured and disposed to reflect varying amounts of the projected light depending upon the angular displacement of the pendulum. The apparatus includes a Moiré encoder configured to project a Moiré pattern of light.

In general, in another aspect, the invention provides a method of evaluating joint mobility of an intact animal joint, the method including providing the intact animal joint and associated condyles, the joint being intact, without having been disarticulated, holding a first condyle associated with the joint stationary, setting a pendulum attached to a second condyle associated with the joint into oscillations, the second condyle oscillating relative to the first condyle about a pivot axis of the joint, monitoring angular displacement of the pendulum while oscillating, and determining, from the monitored angular pendulum displacement, at least one indication of decaying momentum of the pendulum.

Implementations of the invention may include one or more of the following features. The determining comprises calculating an indication of negative acceleration of the pendulum. The determining comprises calculating a coefficient of friction associated with the joint. The providing comprises providing the joint with the synovium intact. The providing comprises providing a di-arthrodial joint stabilized with intra-articular ligaments. The providing comprises providing the joint and associated condyles ex vivo. The method further includes treating the joint before setting the pendulum into oscillations. The treating comprises at least one of genetically engineering the animal and introducing an exogenous agent into the joint.

In general, in another aspect, the invention provides a method of assaying articular lubrication ability in an animal joint, the method including causing a first condyle associated with a first animal joint to oscillate about a pivot axis of the joint relative to a second condyle associated with the first joint, the first joint being intact, without having been disarticulated, determining, from angular displacement over time of the first condyle of the first joint, a first indication of friction associated with the first joint, causing a first condyle associated with a second animal joint to oscillate about a pivot axis of the joint relative to a second condyle associated with the second joint, the second joint being intact, without having been disarticulated, determining, from angular displacement over time of the first condyle of the second joint, a second indication of friction associated with the second joint, and comparing the first and second indications of friction.

Implementations of the invention may include one or more of the following features. The first and second joints are similar types of joints from similar types of animals, and wherein at least the first joint is treated prior to causing its first condyle to oscillate relative to its second condyle. The first joint is treated by introducing an exogenous agent into the first joint. The first joint is from a knockout animal that unable to produce lubricin. The second joint is treated by introducing a synthetic lubricant prior to causing the second joint's first condyle to oscillate relative to the second joint's second condyle. The method further includes weighting the first condyles of the first and second joints with at least approximately an average weight of a type of animal associated with both the first and second joints. The first and second joints are di-arthrodial joints stabilized with intra-articular ligaments.

Various aspects of the invention may provide one or more of the following advantages. Indicia of friction (e.g., coefficient of friction) may be determined for joints of small animals. Indicia of animal joint friction may be determined ex vivo or in vivo. Indicia of animal joint friction may be determined with a high degree of accuracy. Indicia of animal joint friction may be determined autonomously. Relative effects on animal joint friction of various materials, e.g., enzymes, may be determined. Inhibitors may be identified that may reduce increases in friction in animal joints, and thus reduce occurrence or severity of associated health issues, e.g., diseases such as arthritis. Further, friction determination may be carried out on an intact joint. An intact joint is one in which intra-articular ligaments and synovium are present. The joint is excised from an animal and surrounding muscles removed; however, the joint itself remains unbroken, thereby providing an accurate reflection of an in vivo operational state. Earlier methods used completely disarticulated joints in which ligaments supporting the joint were severed and the synovium removed. Native biomechanical properties of the joint, which play a role in its overall function and are important in assessing posited lubricants and compounds, may be preserved.

These and other advantages of the invention, along with the invention itself, will be more fully understood after a review of the following figures, detailed description, and claims.

DETAILED DESCRIPTION OF PREFERRED EMBODIMENTS

Embodiments of the invention provide techniques for determining and evaluating animal joint friction using an articulating joint of an animal, e.g., a rodent such as a mouse or rabbit. Embodiments of the invention provide techniques for assaying articular lubrication ability without disarticulation (articular dislocation). The joint may excised and then tested ex vivo or may be tested in vivo. The invention may be used for di-arthrodial joints stabilized with intra-articular ligaments (e.g., knees, hips, etc.). Exemplary apparatus may be used to test the flexibility and mobility of joints of knock out mice lacking the gene required for lubricating ability, e.g., to analyze synthetic lubricants or other genes posited to play a role in arthritis. Data generated include swing amplitude versus swing cycle number, which can be graphed. Data collection may be expedited with the use of videography, which allows the calculation of pendulum velocity. Measuring pendulum velocity permits the calculation of deceleration, which in turn, is used in calculating a frictional force. The ratio of the frictional force in the joint to the applied normal force is the coefficient of friction. Exemplary methods may be used to evaluate the effect of gene dosing experiments or the inclusion of therapeutic agents in animal feed. For example, an animal is treated, vivisection is performed, and ex vivo testing of the animal's knee joint is undertaken. This represents a significant step forward in preclinical testing of devices and medications. Also, enzymes may be introduced to a joint and the effect(s) of the enzyme studied. If an enzyme is determined to increase the friction in a joint, then efforts may be directed to determining/developing inhibitors of that enzyme, which may in turn improve joint motion and/or reduce, or even eliminate, joint problems such as arthritis. Other embodiments are within the scope and spirit of the invention.

Figure 1:
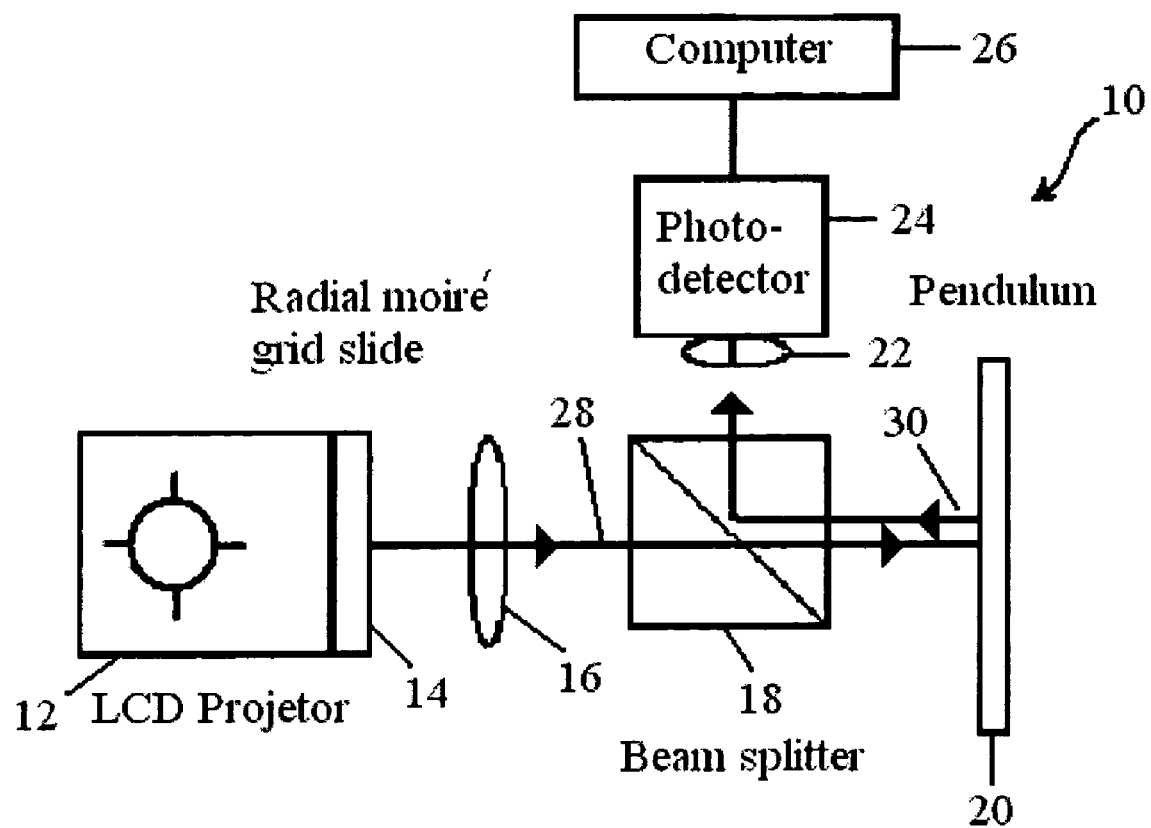
FIG. 1 is a simplified diagram of a system for measuring joint movement and determining joint friction coefficients.

Referring to FIG. 1, a system 10 for determining and analyzing animal joint friction includes an LCD projector 12, a radial Moiré grid slide 14, a lens 16, a beam splitter 18, a pendulum arrangement 20, a lens 22, a photodetector 24, and a computer 26. The system 10 is configured to measure motion associated with an animal joint disposed in the pendulum arrangement 20, analyze that motion to determine velocity of the motion, and use the velocity to determine a coefficient of friction in the joint. The projector 12 is configured to send light toward the arrangement 20 along an incident path 28. The grid slide 14 is disposed in the path 28 and is configured to filter the light provided by the projector 12 into a radially-dependent pattern as explained more fully below. The lens 16 is configured to focus the incident light from the projector 12 and slide 14 into the beam splitter 18. The beam splitter 18 is configured to pass the incident light on the path 28 through to the pendulum arrangement where the light is reflected on a path 30 (e.g., parallel to the path 28). The splitter 18 is further configured to redirect/deflect the light on the path 30 toward the lens 22 and the photodetector 24. The lens 22 focuses the light on the path 30 into the detector 24 that is configured to measure and record the amount of incident light in association with time. The computer 26 is configured to manipulate the measured data to determine a coefficient of friction of the joint, and to compare multiple coefficients of friction.

Figure 2:
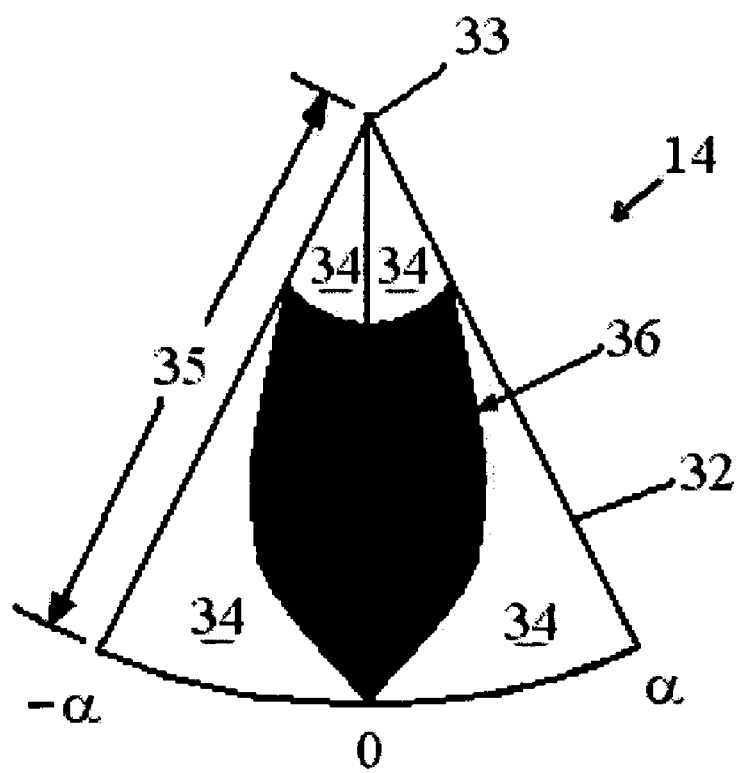
FIG. 2 is a diagram of an exemplary visual indicator for indicating angular position of a pendulum of the system shown in FIG. 1.

Referring to FIG. 2, the radial Moiré grid slide 14 comprises a partially-transparent, partially-opaque member 32. The member 32 is preferably shaped as a sector, but could have other shapes. The sector has a length 35 and is preferably shaped such that it spans an arc from $+\alpha°$ to $-\alpha°$, where $\alpha°$ is the initial angular deflection of the pendulum 20 as discussed below. Other shapes and sizes of the member 32, however, could be used (e.g., with $\alpha°$ being greater than the initial angular deflection). The member 32 includes transparent regions 34 and an opaque region 36. The opaque region 36 is preferably configured as a Moiré pattern, making the projector 12 and the slide 14 a Moiré encoder. This pattern is such that the opaque region 36 extends different radial distances at different angles, with the radial distances being the same for the same magnitude of angle on either side of 0° (i.e., parallel to gravity), e.g., +17° and −17°. The Moiré pattern is projected such that its vertex 33 is disposed along a pivot axis of the pendulum arrangement 20 discussed below. While an analog Moiré pattern may be used, other visual indicators would be acceptable such as a digital indicator (e.g., a bar code with varying codes at different angles). Also, a pattern could be used that uniquely identified the angle's magnitude and side of zero (i.e., the pattern for $+x°$ and $-x°$ would be different).

Figure 3:
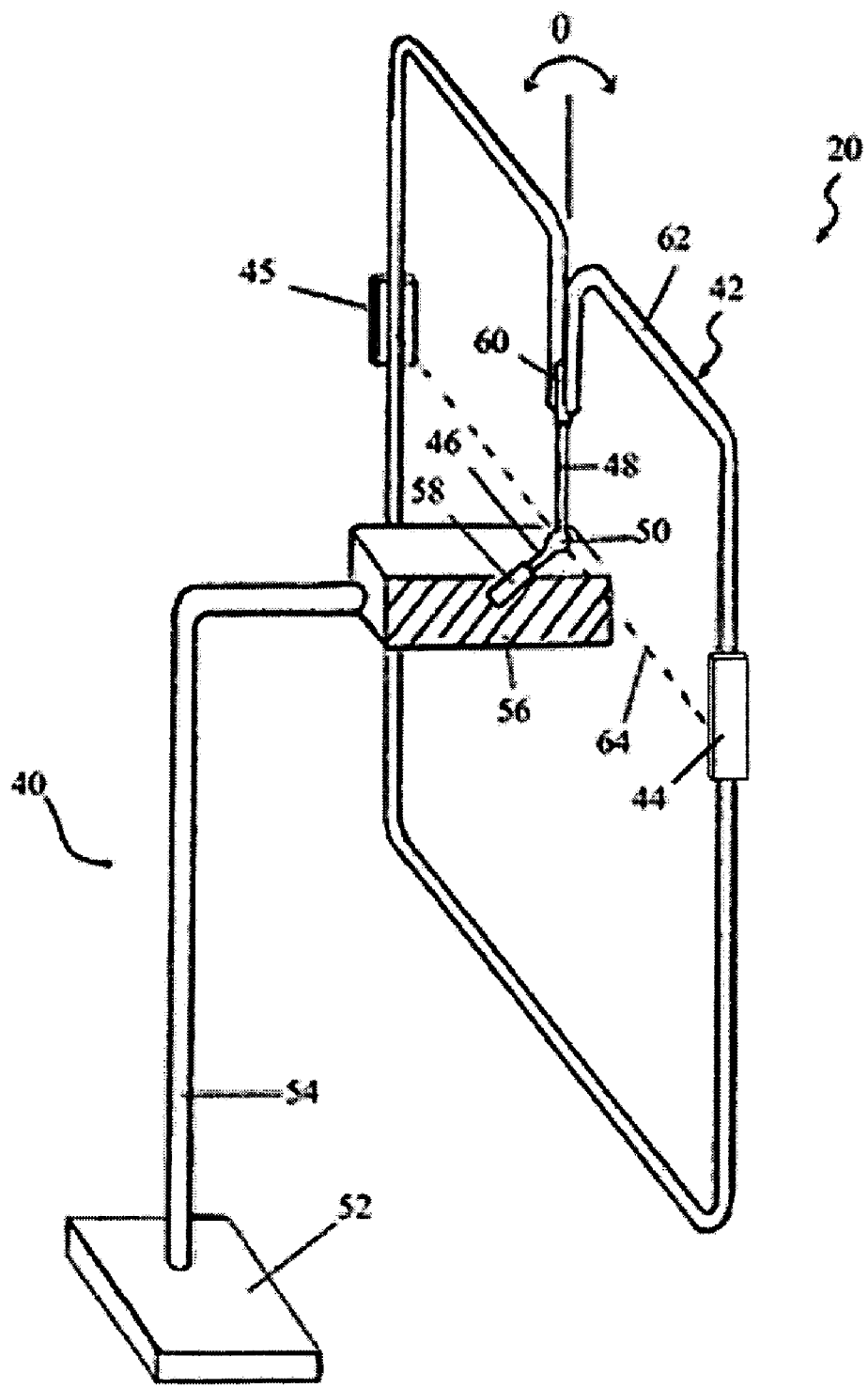
FIG. 3 is a perspective view of a portion of the system shown in FIG. 1 for weighting and holding an animal joint for testing.

Referring to FIG. 3, the pendulum arrangement 20 includes a mounting apparatus 40, a pendulum 42, and a reflector 44. The arrangement 20 is configured to receive and hold a condyle 46, here a tibia, of an animal and to pivot another condyle 48, here a femur, of the animal about an intact joint 50 connecting the two condyles 46, 48. The joint 50 is intact in that its ligaments have not been removed or cut and the synovium of the joint 50 is intact (e.g., the same or substantially the same as it was in vivo), having not been removed, and with the synovial fluid having not be removed (e.g., removed and reinserted in the joint 50 or replaced with different synovial fluid), although the muscles and tendons are preferably removed. Keeping the synovium intact maintains the bearing surface congruity.

The mounting apparatus 40 includes a base 52, an arm 54, and a stabilizing block 56. The base 52 is configured to provide support to the arm 54 that is coupled to the base and the stabilizer 56. The stabilizer 56, e.g., a plexiglass block, is shown partially cutaway and is configured to receive and retain the lower, immobile condyle 46, here at an angle of approximately 45° relative to gravity. In particular, the stabilizer 56 shown is configured to receive and hold a tube 58 (e.g., made of plexiglass) that is configured to fit over an end of, and be secured to (e.g., with a press fit), the condyle 46 and to be inserted into a hole or other receptacle in the block 56. The block 56 is configured to hold the condyle 46 stationary during use of the arrangement 20 to move the condyle 48 relative to the condyle 46 about the joint 50.

The pendulum 42 includes a condyle tube 60 and a frame 62. The tube 60 is configured to fit over an end of, and be secured to (e.g., with a press fit), the upper, movable condyle 48. The tube 60 is fixedly attached to the frame 62. The frame 62 is preferably configured to weigh approximately the same as the animal from which the condyles 46, 48 and the joint 50 were taken. For example, the frame 62 may weigh approximately the same as an adult mouse or rabbit. The frame 62 can thus load the joint 50 similarly to the load experienced by the joint 50 in vivo. Weights in addition to the frame 62 itself may be coupled to the frame 62, but are preferably added symmetrically about either side of the pivot axis 64 and each side of the frame 62 relative to the axis of the upper, movable condyle 48. The frame 62 is symmetrically shaped about an axis of the condyle 48 and configured to have approximately one-third of its length above, and approximately two-thirds of its length below, a pivot axis 64 of the joint 50. With this arrangement, the pendulum can be deflected angularly about the pivot axis 64 and released, and will cyclically sway about the axis 64 until coming to rest due to friction in the joint 50.

Attached to the frame 62 is the reflector 44. The reflector 44 is preferably configured as a relatively narrow, e.g., approximately 1 mm wide, linear reflector along the axis of the frame 62. With a thin reflector, varying amounts of light incident upon the reflector from the projector 12 (FIG. 1) will be reflected as the angle of the frame 62 varies due to the projected angle-varying light pattern, here a Moiré pattern. The reflector 44 is disposed symmetrically (at least with respect to weight) about the pivot axis 64, with a light-reflective portion the reflector 44 being disposed to receive and reflect incident light from the projector 12 (i.e., extending downward from the pivot axis at least the length 35 of the Moiré pattern). A counterweight 45 is provided on the opposite side of the frame 62 from the reflector 44 to help ensure balanced motion of the pendulum 42.

Referring also to FIG. 1, the photodetector 24 is configured to receive and record indicia of the light reflected from the reflector 44. The detector 24 includes a light-sensitive apparatus such as a charge coupled device (CCD) that receives and converts photons into electrical signals representative of the amount of light received. The indicia of the amount of light received is stored in association with the time that it was received.

The computer 26 is configured to process the indicia of light measured by the photodetector 24 to determine the coefficient of friction $\mu$ of the joint 50. The computer 26, or at least its functionality with respect to determining $\mu$, can be incorporated into the detector 24. The computer 26 is configured to calculate the decay in momentum at the joint 50 as the upper condyle 48 oscillates from its initial deflection amount to zero. The computer 26 includes appropriate software and a processor for executing instructions in that software to determine $\mu$ (and to perform other functions as discussed). The computer 26 is configured to calculate $\mu$ by determining deceleration (negative acceleration) of the pendulum 42 according to: $a=dv/dt$. Velocity is determined from $V=(2gh)^{1/2}$ where h is the height from where the pendulum 42 reaches apogee to the point of maximum velocity at $\alpha=0$, and g is gravitational acceleration constant. The frictional force, $F_f$, acting on the pendulum 42 at the articular surface is equated to $\mu W$, where W is the normal force. The computer 26 uses a ratio of acceleration terms to calculate $\mu$ according to: $\mu = F_f/W = a/g$. The computer 26 is configured to neglect aerodynamic drag (e.g., of the upper condyle 48 and the pendulum 42) and to assume g to be 9.81 m/sec$^2$, but drag may be considered if desired, and a different value for g may be used.

Figure 4:
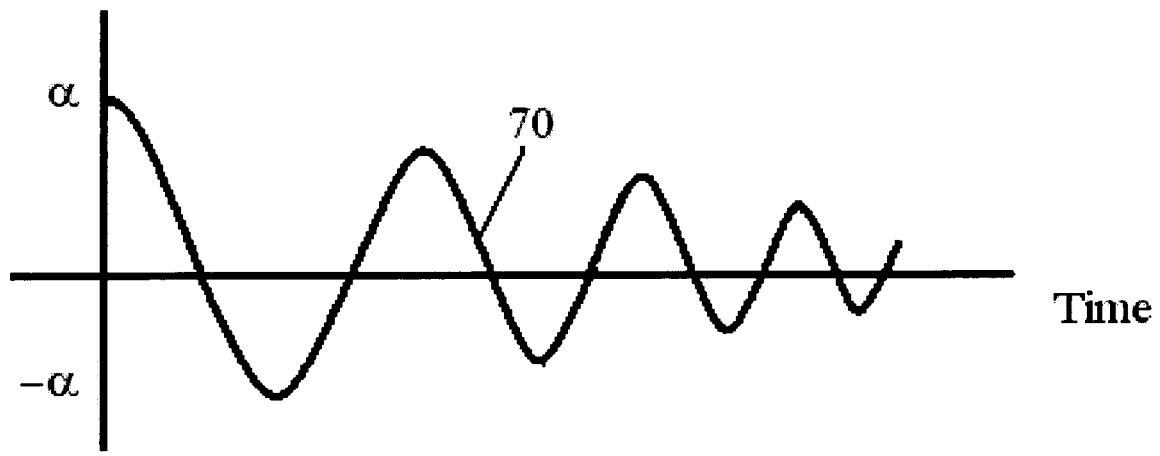
FIG. 4 is a plot of angular displacement of the pendulum of the system shown in FIG. 1 versus time.

Referring also to FIG. 4, the computer 26 can produce a plot 70 of the angular displacement of the pendulum 42 over time. As shown by the plot 70, the displacement decreases over time due to friction in the joint 50, with a corresponding decrease in pendulum velocity and thus momentum. From this plot 70, the computer 26 can calculate the pendulum angular velocity (related to momentum) and the angular acceleration a. Knowing the acceleration a, the computer 26 calculates the coefficient of friction of the joint 50 according to $\mu=a/g$. The computer 26 may calculate the desired values using the appropriate data but without producing a plot.

Other system configurations are within the scope of the invention. For example, referring to FIGS. 1, 3, and 5, the pendulum arrangement 20 could be replaced with the arrangement 72 shown in FIG. 5. In the arrangement 72, the angular displacement of the pendulum (the pendulum frame is not shown in FIG. 5) is determined by observing (e.g., with video recording equipment, not shown) the upper condyle 48 relative to a protractor 74 or other angle-indicating device. Still other configurations of pendulum arrangements are within the scope of the invention.

Figure 6:
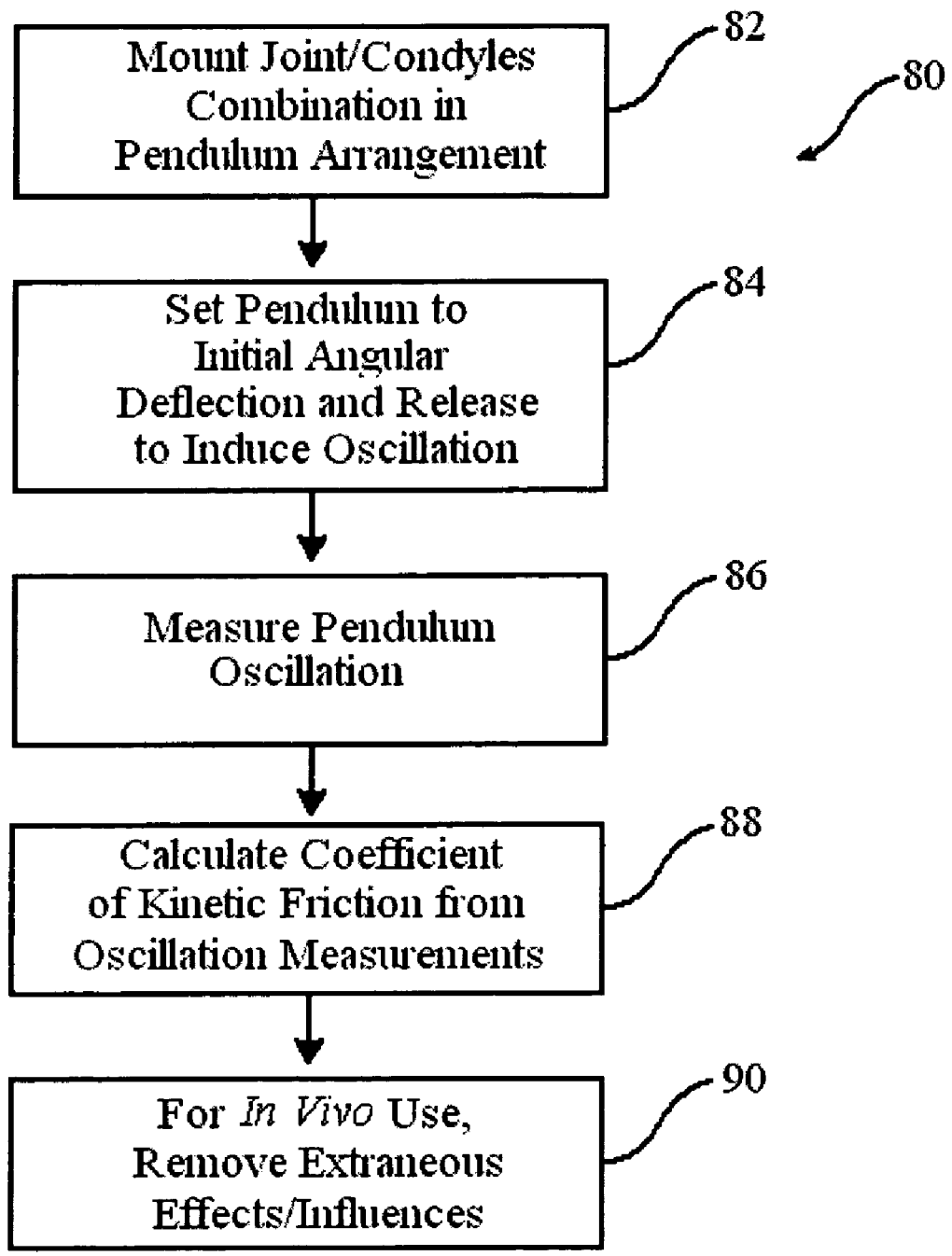
FIG. 6 is a block flow diagram of a process of determining joint friction using the system shown in FIG. 1.

In operation, referring to FIG. 6, with further reference to FIGS. 1-4, a process 80 for analyzing joint friction of a joint with intact ligaments and an intact synovium using the system 10 includes the stages shown. The process 80, however, is exemplary only and not limiting. The process 80 may be altered, e.g., by having stages added, removed, or rearranged.

At stage 82, an intact joint with its associated bones is mounted in the pendulum arrangement 20. The tube 58 is slid over and fixedly connected to the lower condyle 46. The tube 58 with the inserted condyle 46 is fixedly attached to the block 56 such that the joint 50 allows free movement of the upper condyle 48. The tube 60 of the pendulum 42, with the frame 62 coupled to the tube 60, is slid onto and fixedly connected to the upper condyle 48. For example, a mouse knee joint may be used, with the lower condyle 46 being a mouse tibia, the upper condyle 48 being the mouse femur, and the joint 50 being the intact mouse knee.

At stage 84, the pendulum 42 is moved to an initial deflection position and released to induce decaying oscillation of the pendulum 42. The pendulum 42 is pivoted about the pivot axis 64 to an initial angular position $\theta=\alpha$ (either positive or negative). Upon its release, the pendulum 42 will oscillate in $\theta$ about the pivot axis 64, with friction of the joint 50 causing the oscillation to decay until the pendulum 42 stops oscillating.

At stage 86, the oscillations of the pendulum 42 are measured. The projector 12 shines light through the Moiré grid slide 14. The angle-dependent pattern of light passes along the path 28 through the lens 16 and the beam splitter 18 to the pendulum arrangement 20. The light hits the reflector 44 that reflects a thin slice of the projected pattern of light along the path 30. The reflected light is directed by the beam splitter 18 through the lens 22 to the detector 24. The detector 24 receives the light photons and provides indicia of the amount of light received. The amounts of light received over time are recording in conjunction with the time that the various light amounts are received.

At stage 88, the computer 26 determines the coefficient of friction of the joint 50. The computer 26 analyzes the angular deflection of the pendulum frame 62 over time to determine the pendulum velocity and acceleration. The decay in the pendulum acceleration, and thus decay in the pendulum momentum, is used to determine the coefficient of kinetic friction in the joint 50.

At stage 90, if this is an in vivo test, then effects of muscle, tendons, etc. are removed from the determined coefficient of friction. The computer 26 relates, e.g., normalizes (e.g., by taking a ratio), the determined coefficient of friction to a baseline coefficient of friction. The baseline coefficient of friction may be the coefficient of a knockout animal's joint 50 (i.e., a mouse genetically altered not to produce joint lubrication) determined with the muscles and tendons associated with the joint 50 intact. This baseline coefficient is preferably determined from an in vivo test of the mouse. Alternatively, a baseline coefficient could be determined by injecting a proteolytic enzyme into a mouse to eliminate the joint lubricant before determining the coefficient of friction of the joint.

Figure 7:
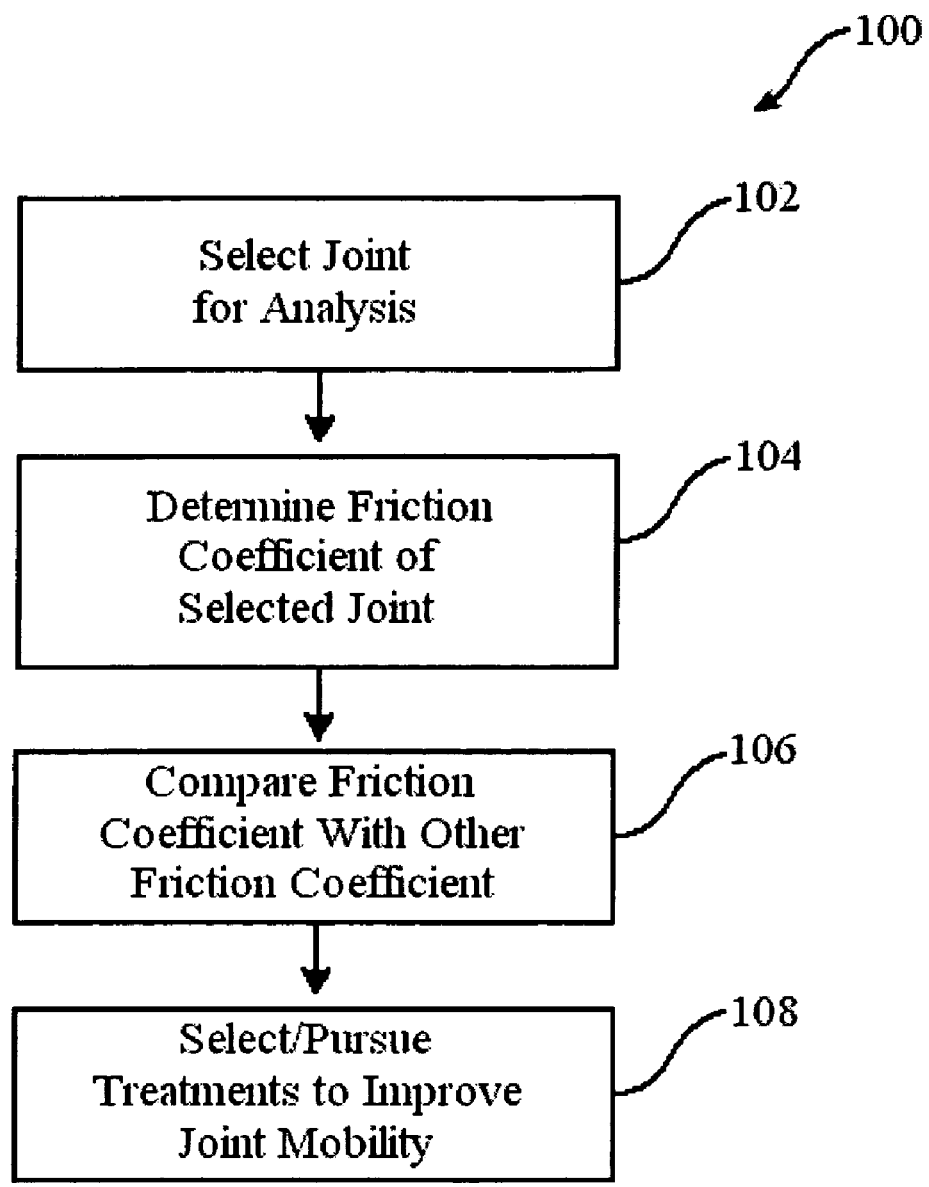
FIG. 7 is a block flow diagram of a process of determining effects of different influences on joint mobility.

In use, referring to FIG. 7, with further reference to FIGS. 1-4, a process 100 for determining effects on joint friction of various influences (human-induced and otherwise) using the system 10 includes the stages shown. The process 100, however, is exemplary only and not limiting. The process 100 may be altered, e.g., by having stages added, removed, or rearranged.

At stage 102, a first joint is selected for analysis. The selected joint may be treated or untreated. Untreated joints do not have, and have not had, exogenous agents applied to them and have not been otherwise artificially altered. Untreated joints may, however, not be ideal in the sense that the joints may be negatively affected by natural causes such as arthritis. Treated joints have or have had an exogenous agent or agents applied to them, or have been otherwise artificially altered, e.g., by genetic engineering (e.g., knockout animals). Exogenous agents may be synthetic lubricants or enzymes that are posited to have an effect upon joint lubrication (e.g., affect the production or quality of lubricin in a joint).

At stage 104, the coefficient of friction of a first joint (including associated condyles) is determined. The joint, be it treated or untreated is mounted in the pendulum arrangement 20 and the system is used in accordance with the process 80 described above to determine the joint's coefficient o friction.

At stage 106, the friction coefficient determined at stage 104 is compared with other friction coefficients. The comparison is used to determine what effect a treatment (e.g., exogenous agent such as an enzyme or a genetic alteration) has on joint mobility. For example, coefficients of friction for treated joints that are lower than that of joints with similar characteristics except for the treatment applied to the treated joint indicate potentially useful treatments for increasing joint mobility. Likewise, coefficients of friction for treated joints that are higher than that of joints with similar characteristics except for the treatment applied to the treated joint indicate treatments that are deleterious for increasing joint mobility and should be avoided.

At stage 108, candidates for further research are selected and possibly pursued for improving the mobility of joints (e.g., increasing joint mobility or delaying/inhibiting decreases in joint mobility). Based on the treatments that show potential for increasing joint mobility, further research can be performed. For example, if friction analysis indicates that introduction of a particular enzyme into a joint decreases that joint's mobility (e.g., range/extent of motion or ease of motion), then research can be pursued to find biologically compatible inhibitors of that enzyme. Further, if the friction analysis indicates that a particular synthetic lubricant increases joint mobility, then that lubricant can be pursued for use in humans.

Other embodiments are within the scope of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Experiments: Evaluation of Joint Mobility by Pendulum Movement

Techniques described herein provide for more versatile and accurate evaluation of joint mobility. Amplitude of swing was measured using a protractor (FIG. 5).

Analysis of Frictional Characteristics of Mouse Joints: an Animal Model for Arthritic Disease Lubricating ability was measured in resected murine knee joints ex vivo to determine if the CACP phenotype included a lack of diarthrodial lubrication.

A CACP Knockout Mouse Model was generated as follows. Embryonic stem cell targeting by homologous recombination was used to generate Prg4 knockout mice. These mice were made and have been maintained on the 129SvEv inbred mouse strain. Absence of Prg4 mRNA and protein in the knockout mice was confirmed by Northern and Western blotting. Histologic features in knockout mouse joints recapitulate features that have been described in patients with CACP.

Figure 5:
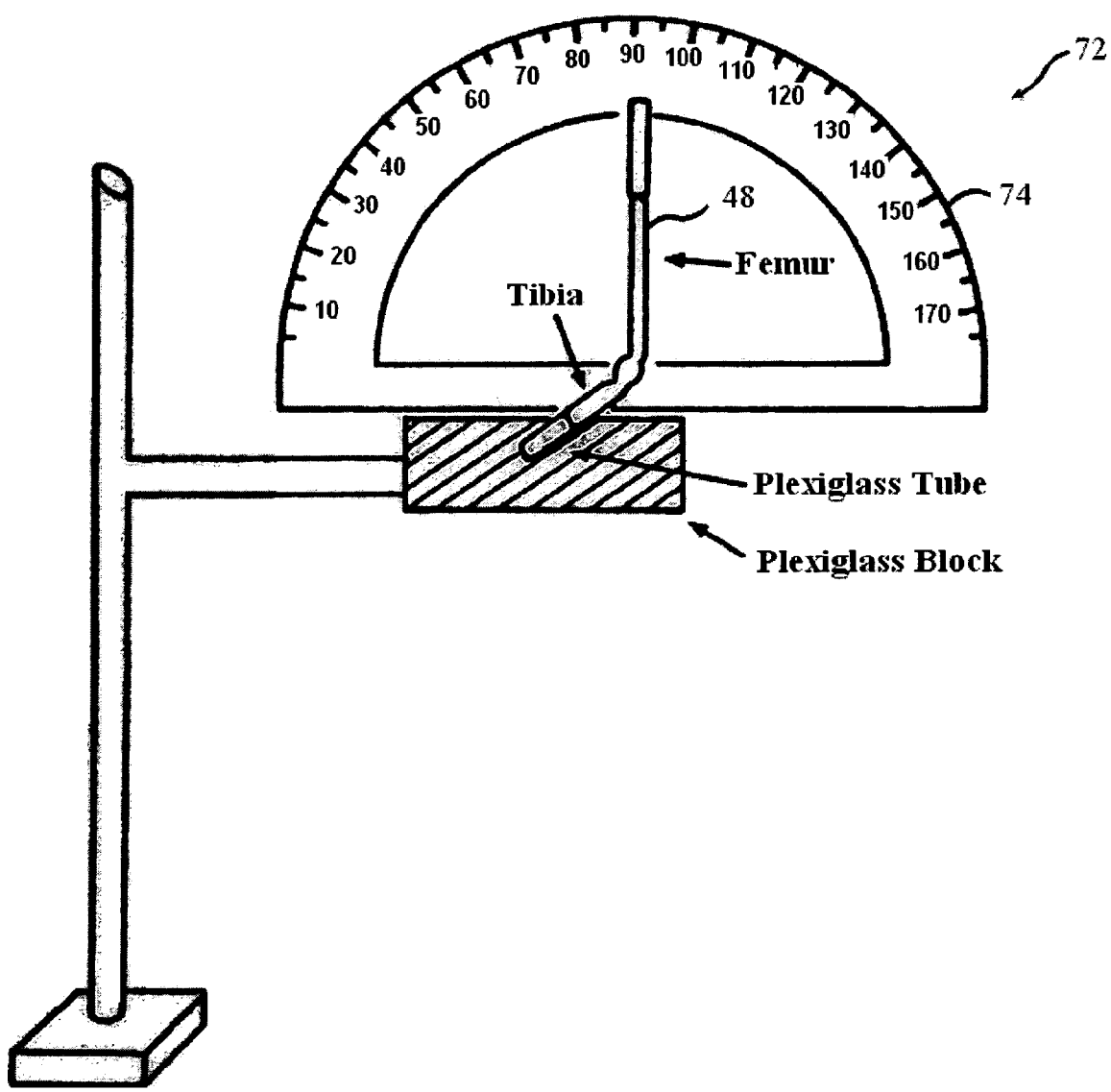
FIG. 5 is a simplified diagram of an alternative pendulum arrangement for use in the system shown in FIG. 1.

A joint motion pendulum simulator assembly (e.g., as shown in FIGS. 1 and 5) was used to evaluate mobility. The value of $\mu$ of a weight bearing joint was measured by excising the joint and centering it in the axis of rotation of a pendulum. Decrease in the amplitude of swing was proportional to the loss of energy as the pendulum transitions from pure potential to kinetic energy. By knowing the normal (perpendicular) load applied to the joint, the coefficient of friction was calculated as a ratio of the decrease in pendulum velocity to the earth's gravitational constant g. This simple calculation neglected aerodynamic drag and assumed g to be 9.81 m/sec2. The severed ends of the femur and tibia were fitted with rigid plastic tubing. The tibial end was supported at 45° off the perpendicular by an experimental test stand. The femur end supported a pendulum, which hung below the excised joint. The mass of the pendulum was 20 gm, roughly that of an adult mouse. The pendulum was set in motion at a=30° off the perpendicular while being videotaped. A protractor was situated behind the joint. The pendulum was supported by the upper condyle connected to a moment of the pendulum just long enough to serve as an indicator against the protractor. Sweep of the lower pendulum, measured in degrees, was indicated by the corresponding but opposite movement of the upper moment. Data was collected until the pendulum came to rest. Frame by frame post hoc video analysis was performed to identify the points of maximal pendulum excursion. Pendulum amplitude in degrees was plotted against cycle number. Prior to the study of CACP KO mice, normal murine knee joints were trypsinized to demonstrate proof of concept.

Statistical Analysis was carried out as follows. Regression models of amplitude versus cycle # for each limb type were compared by a test for equality of regression coefficients (Stata, College Station, Tex.). Significance level was established at $p=0.05$ a priori. This analysis looked for divergence of the data via equality of regression coefficients.

Figure 8:
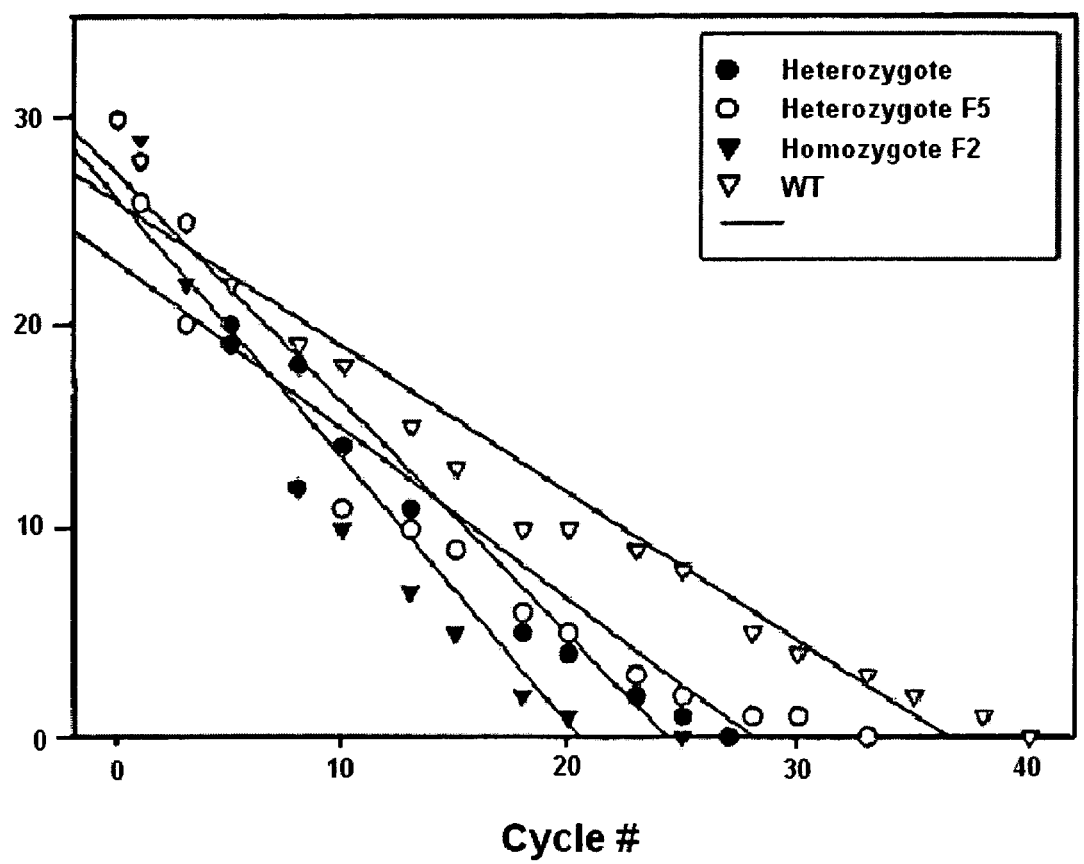
FIG. 8 is a graph showing maximum angular displacement over time of knee joints from various mice.

Knee joints from 11 month old CACP KO mouse homozygotes, heterozygotes and the appropriate genetic background wild type (WT) control were studied in the joint motion pendulum simulator. Regression of amplitude versus cycle# for each limb type was performed (FIG. 8). Homozygote KO and WT limbs were significantly different. [F (2,25)=33.6; p<0.0001]. Both heterozygote KO limbs were also significantly different from the WT control [F (2,42)=17.4; p<0.0001]. Both heterozygote KO limbs were also significantly different from the homozygote KO limb [F (2,35) =10.3; p=0.0003]. Finally, the heterozygote KO limbs were also significantly different from each other [F (2,24)=3.7; p=0.038].

Values of $\mu$ for a homozygote KO mouse limb were the highest (Table 1). By contrast the WT control limb demonstrated the lowest $\mu$.

TABLE 1

| | Homozygote ▼ | Heterozygote ○● | WT △ |
|---|---|---|---|
| μ | 0.0031 | 0.0021-0.0027 | 0.0018 |

These data indicate that joint lubrication is mediated by superficial zone protein and lubricin. These molecules occupy the lamina splendens and keep apposed and flattened articular cartilage asperities separated, thus avoiding wear. CACP is an arthropathy due, in part, to lack of lubrication affecting tendons, weight bearing joints and the pericardium. The amplitude versus cycle # relationships generally appeared linear indicating boundary lubrication. The pendulum decreased by the same proportion with each swing. Friction was found to be independent of sliding speed. By contrast, a hydrodynamic lubricant would become thicker at slower speeds, restraining the bearing surfaces and moving progressively smaller amounts. The observed values of $\mu$ are consistent with earlier observations using a pendulum technique in a cadaveric human ankle joint, e.g., $\mu$ values in the range of 0.005-0.024.

What is claimed is:

1. A method for evaluating the effect of therapeutic intervention on joint mobility of an intact animal joint, the method comprising:

providing said intact animal joint and associated condyles, wherein said joint has an intact synovium and has not been disarticulated;

introducing an exogenous agent into said joint;

holding a first condyle associated with said joint stationary;

setting a pendulum attached to a second condyle associated with said joint into oscillation, said second condyle oscillating relative to said first condyle about a pivot axis of said joint;

monitoring angular displacement of said pendulum while oscillating; and determining from said displacement at least one indicium of momentum decay of said pendulum, wherein the determination, from said at least one indicium, of a decrease in said momentum decay of said pendulum in said treated joint relative to momentum decay in a non-treated joint indicates said exogenous agent improves joint mobility.

2. The method of claim 1, wherein said determining comprises calculating an indication of negative acceleration of said pendulum.

3. The method of claim 2, wherein said determining comprises calculating a coefficient of friction associated with said joint.

4. The method of claim 1, wherein said joint is diarthrodial and stabilized with intra-articular ligaments.

5. The method of claim 1, wherein said joint and associated condyles are ex vivo.

6. The method of claim 1, further comprising testing said joint mobility prior to introducing said exogenous agent.

7. The method of claim 1, wherein said animal joint is obtained from a genetically-altered animal.

8. The method of claim 1, wherein said exogenous agent is a compound that reduces a symptom of an arthritic disease.

9. The method of claim 1, wherein said exogenous agent is a synthetic lubricant or an enzyme.

10. The method of claim 1, wherein said exogenous agent is superficial zone protein or lubricin.

11. The method of claim 1, wherein said exogenous agent is a compound that inhibits an enzyme that decreases joint mobility.

* * * * *